(12) United States Patent
Ouchi

(10) Patent No.: US 6,238,336 B1
(45) Date of Patent: May 29, 2001

(54) ULTRASONIC ENDOSCOPE INCLUDING RADIAL SCANNING AND LINEAR SCANNING ULTRASONIC TRANSDUCERS

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/258,313

(22) Filed: Feb. 26, 1999

(30) Foreign Application Priority Data

Mar. 4, 1998 (JP) .................................................. 10-051582

(51) Int. Cl.[7] ................................. A61B 1/04; A61B 8/12
(52) U.S. Cl. .......................... 600/160; 600/104; 600/463; 600/113
(58) Field of Search ..................................... 600/439, 461, 600/462, 160, 109, 104, 463, 113, 129

(56) References Cited

U.S. PATENT DOCUMENTS

| | | |
|---|---|---|
| 4,433,692 | 2/1984 | Baba . |
| 4,605,009 * | 8/1986 | Pourcelot et al. .................... 600/109 |
| 4,757,819 * | 7/1988 | Yokoi et al. .......................... 600/156 |
| 4,974,590 * | 12/1990 | Saito ..................................... 600/462 |
| 5,471,988 * | 12/1995 | Fujio et al. ........................... 600/439 |
| 5,492,126 * | 2/1996 | Hennige et al. ...................... 600/439 |
| 5,596,989 | 1/1997 | Morita . |
| 5,873,828 * | 2/1999 | Fujio et al. ........................... 600/439 |
| 5,980,454 * | 11/1999 | Broome ................................ 600/176 |

FOREIGN PATENT DOCUMENTS

| | | |
|---|---|---|
| 2553506 | 12/1991 | (JP) . |
| 8-126643 | 5/1996 | (JP) . |

* cited by examiner

Primary Examiner—John P. Leubecker
(74) Attorney, Agent, or Firm—Greenblum & Bernstein, P.L.C.

(57) ABSTRACT

An ultrasonic endoscope includes: an objective optical system provided at a tip portion of the ultrasonic endoscope; a treatment tool insertion channel provided along the ultrasonic endoscope, the treatment tool insertion channel having an exit opening at the tip portion; a linear-scanning ultrasonic transducer, provided at the tip portion, for scanning a first scanning plane section which lies on a plane including a shaft axis of the tip portion; and a radial-scanning ultrasonic transducer, provided at the tip portion, for scanning a second scanning plane section which lies on a rotational plane about the shaft axis. The linear-scanning ultrasonic transducer and the radial-scanning ultrasonic transducer are positioned so that the first scanning plane section intersects the second scanning plane section within an optical field of the objective optical system, and wherein the treatment tool insertion channel is formed so that the tip of an tubular instrument, inserted into the treatment tool insertion channel, projects outwards from the exit opening to pass an intersection between the first scanning plane section and the second scanning plane section.

20 Claims, 2 Drawing Sheets

ULTRASONIC ENDOSCOPE INCLUDING RADIAL SCANNING AND LINEAR SCANNING ULTRASONIC TRANSDUCERS

BACKGROUND OF THE INVENTION

1. Field of the Invention

The present invention relates to an ultrasonic endoscope, both an objective optical system for optical observation and an ultrasonic transducer being incorporated into the tip of the endoscope.

2. Description of the Related Art

Endoscopic ultrasonography (EUS) is a combination of endoscopy and ultrasonography, a small ultrasonic transducer (ultrasonic probe) being incorporated into the tip of an endoscope. Two different instrument types of EUS are currently available: a linear-type echo endoscope (providing an ultrasonic view which extends parallel to the shaft axis of the instrument) and a radial-type echo endoscope (providing a 360° ultrasonic panoramic view which extends perpendicular to the shaft axis of the instrument). These types each have merits and demerits and are thus selectively used depending on the circumstances.

EUS is used for taking ultrasonic tomograms or plane sectional images of, e.g., a viscera or part of a viscera which is located at the back or behind a mucous membrane. When the EUS is used in an endoscope, a needle (an aspiration needle or an injection needle) which is introduced into the body through a treatment tool insertion channel is penetrated into a target part through a mucous membrane. In this case, when the radial-type echo endoscope is used, the course of the needle cannot be monitored since only a small part of the whole image of the needle appears in any plane sectional images, so that the penetration depth cannot be monitored. Therefore, an operation using the radial-type echo endoscope cannot be said to be performed with safety. On the other hand, when the linear-type echo endoscope is used, the course of the needle can be monitored since the needle is guided in an ultrasonic scanning surface therealong, so that the penetration depth can be clearly monitored. However, since any other plane sectional images of the surroundings of the penetrated portion cannot be monitored at all, while the plane sectional image of the penetrated portion is monitored, it is difficult to make sure if the penetrated portion is actually an appropriate portion to be penetrated by the needle.

SUMMARY OF THE INVENTION

The primary object of the present invention is to provide an ultrasonic endoscope with which the needle can be properly and accurately penetrated into a target part while accurately monitoring the state of penetration in a plane sectional image.

To achieve the object mentioned above, according to an aspect of the present invention, there is provided an ultrasonic endoscope that includes: an objective optical system provided at a tip portion of the ultrasonic endoscope; a treatment tool insertion channel provided along the ultrasonic endoscope, the treatment tool insertion channel having an exit opening at the tip portion; a linear-scanning ultrasonic transducer, provided at the tip portion, for scanning a first scanning plane section which lies on a plane including a shaft axis of the tip portion; and a radial-scanning ultrasonic transducer, provided at the tip portion, for scanning a second scanning plane section which lies on a rotational plane about the shaft axis, wherein the linear-scanning ultrasonic transducer and the radial-scanning ultrasonic transducer are positioned so that the first scanning plane section intersects the second scanning plane section within an optical field of the objective optical system, and wherein the treatment tool insertion channel is formed so that the tip of an tubular instrument, inserted into the treatment tool insertion channel, projects outwards from the exit opening to pass an intersection between the first scanning plane section and the second scanning plane section.

Preferably, the ultrasonic endoscope further includes a display (e.g., a TV monitor) for simultaneously displaying a first image obtained through the linear-scanning ultrasonic transducer and a second image obtained through the radial-scanning ultrasonic transducer.

Preferably, the ultrasonic endoscope further includes a device for moving the tip of the tubular instrument, which projects outwards from the exit opening, in a direction along the intersection.

Preferably, the moving device includes a rotatable member which is positioned in the vicinity of the exit opening to abut against the tip of the tubular instrument.

Preferably, the linear-scanning ultrasonic transducer and the radial-scanning ultrasonic transducer are arranged adjacent to each other so that the radial-scanning ultrasonic transducer is positioned closer to the top of the tip of the ultrasonic endoscope than the linear-scanning ultrasonic transducer.

Preferably, the radial-scanning ultrasonic transducer is positioned so that the second scanning plane section is inclined rearwardly by a predetermined angle with respect to the shaft axis, wherein the objective optical system is positioned so that the optical field of the objective optical system covers both the first scanning plane section and the second scanning plane section.

Preferably, the linear-scanning ultrasonic transducer is positioned between the radial-scanning ultrasonic transducer and the objective optical system, the objective optical system being positioned to extend an optical axis thereof forwardly towards the intersection.

Preferably, the objective optical system includes a shield glass which is fixed to the tip portion adjacent to the exit opening.

Preferably, the shield glass is inclined by a predetermined angle with respect to the shaft axis to face the intersection.

According to another aspect of the present invention, there is provided an ultrasonic endoscope that includes: an objective optical system provided at a tip portion of the ultrasonic endoscope; a treatment tool insertion channel provided along the ultrasonic endoscope, the treatment tool insertion channel having an exit opening at the tip portion; a radial-scanning ultrasonic transducer, provided at the tip portion, for scanning one scanning plane section which lies on a rotational plane about a shaft axis of the tip portion; and a linear-scanning ultrasonic transducer, provided at the tip portion to be positioned between the exit opening and the radial-scanning ultrasonic transducer, for scanning another scanning plane section which lies on a plane including the shaft axis, wherein the linear-scanning ultrasonic transducer and the radial-scanning ultrasonic transducer are positioned so that the one scanning plane section intersects the another scanning plane section within an optical field of the objective optical system, and wherein the treatment tool insertion channel is formed so that the tip of an tubular instrument, inserted into the treatment tool insertion channel, projects outwards from the exit opening to pass an intersection between the one scanning plane section and the another scanning plane section.

The present disclosure relates to subject matter contained in Japanese Patent Application No.10-51582 (filed on Mar. 4, 1998) which is expressly incorporated herein by reference in its entirety.

BRIEF DESCRIPTION OF THE DRAWINGS

The present invention will be described below in detail with reference to the accompanying drawings in which.

DESCRIPTION OF THE PREFERRED EMBODIMENT

Figure 1:
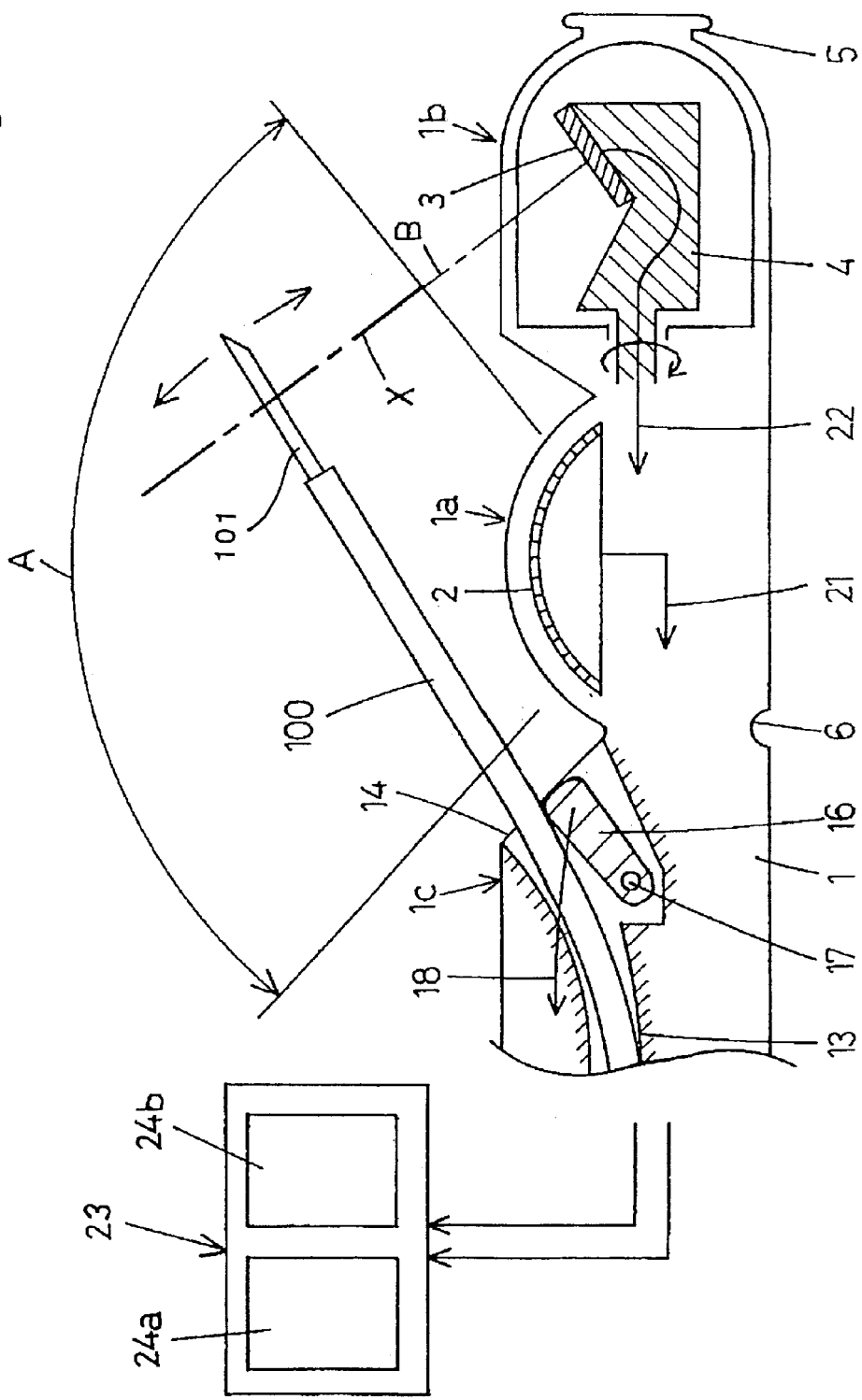
FIG. 1 is a cross sectional view of the tip of an ultrasonic endoscope to which the present invention is applied.

As shown in FIG. 1, a tip portion (distal end) 1 of an ultrasonic endoscope of the EUS is provided with a linear scanning portion 1a for scanning a scanning plane section "A" which lies on a plane including a shaft axis O (see FIG. 2) of the tip portion 1. The linear scanning portion 1a is provided inside the tip portion 1 with a linear-scanning ultrasonic transducer (linear-scanning ultrasonic probe) 2 which is made of an array of ultrasonic-generating oscillators. Accordingly, the linear-scanning ultrasonic transducer 2 is arranged so as to provide an ultrasonic view parallel to the shaft axis O.

The tip portion 1 is further provided with a radial scanning portion 1b for scanning a scanning plane section "B" which lies on a rotational plane "B" about the shaft axis O. The linear scanning portion 1a and the radial scanning portion 1b are arranged adjacent to each other so that the radial scanning portion 1b is closer to the top of the tip portion 1 than the linear scanning portion 1a. The radial scanning portion 1b is provided inside the tip portion 1 with a radial-scanning ultrasonic transducer (radial-scanning ultrasonic probe) 3 which is made of an array of ultrasonic-generating oscillators. Accordingly, the radial-scanning ultrasonic transducer 3 is arranged so as to provide a 360° ultrasonic panoramic view perpendicular to the shaft axis O. It can be understood from the foregoing that the ultrasonic endoscope of EUS of the present embodiment is a hybrid type ultrasonic endoscope: a combination of a linear type and a radial type.

The radial-scanning ultrasonic transducer 3 is fixed onto a rotatable base 4 provided inside the tip portion 1. The rotatable base 4 is rotated about the shaft axis O. As can be seen in FIG. 1 the radial-scanning ultrasonic transducer 3 is fixed to the rotatable base 4 to be inclined rearwardly by a predetermined angle with respect to the shaft axis O so that the scanning plane section "B" intersects the scanning plane section "A". In each of FIGS. 1 and 2 "X" represents an intersection between the scanning plane section "A" and the scanning plane section "B". The intersection "X" is in the shape of a straight line.

The tip portion 1 is provided around the shaft axis O with front and rear annular grooves 5 and 6 to which a rubber band (not shown) for fixing a balloon is secured. The front groove 5 is formed at the top of the tip portion 1, while the rear groove 6 is formed around a portion of the tip portion 1 at the back of the linear scanning portion 1a with respect to the tip portion 1 (see FIG. 2).

The tip portion 1 is further provided at the back of the rear groove 6 with an objective optical viewing portion (objective optical system) 1c which includes a shield glass 11 and an objective optical lens (not shown) provided inside the shield glass 11. The shield glass 11 is fixed to the tip portion 1 to be inclined by a predetermined angle with respect to the shaft axis O so as to face the intersection "X". Hence, the objective optical viewing portion 1c is positioned to extend an optical axis thereof forwardly towards the intersection "X".

Figure 2:
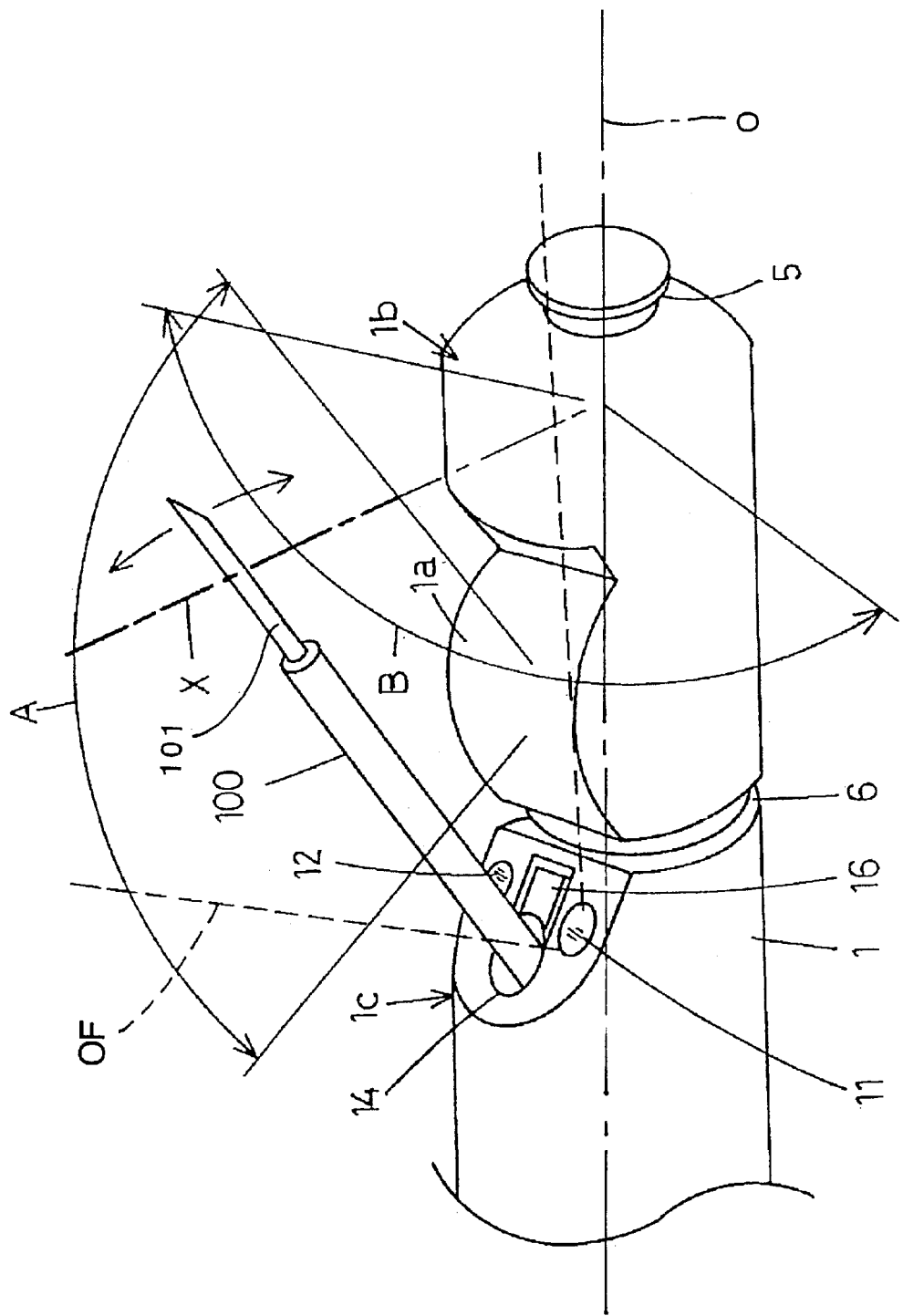
FIG. 2 is a perspective view of the tip of the ultrasonic endoscope shown in FIG. 1.

The optical field of the shield glass 11 is shown by dotted lines in FIG. 2. It can be appreciated from FIG. 2 that the optical field OF covers both the scanning plane section "A" of the linear-scanning ultrasonic transducer 2 and the scanning plane section "B" of the radial-scanning ultrasonic transducer 3. The tip portion 1 is further provided, in the vicinity of the shield glass 11 with another shield glass 12 from which illumination light is emitted towards a viewing area.

The tip portion 1 is further provided, between the two shield glasses 11 and 12, with an exit opening 14 of a treatment tool insertion channel 13. The tip portion of a tubular instrument 100 having a needle (an aspiration needle or an injection needle) 101 at its point projects outwards from the exit opening 14.

The tip portion 1 is further provided inside the exit opening 14 with a rotatable member 16 which is pivoted at a shaft 17 extending in a direction substantially perpendicular to the shaft axis O. The rotatable member 16 abuts against the instrument 100 and is manipulated to rotate about the shaft 17 by a manipulating device (not shown) to swing the tip (needle 101) of the instrument 100.

The tip of the instrument 100 is oriented so that the projecting direction thereof lies in a plane which includes the scanning plane section "A" of the linear-scanning ultrasonic transducer 2 and passes the intersection "X". By manipulating the rotatable member 16, the projecting direction of the tip of the instrument 100 can be varied so that the tip of the instrument 100 moves along the intersection "X". In other words, rotation of the rotatable member 16 causes the needle 101 to swing along the intersection "X".

In the EUS having the aforementioned structure, optical images are viewed through an eyepiece (not shown) via the shield glass 11 and the aforementioned objective optical lens (not shown), which is positioned inside the shield glass 11. On the other hand, signals which are output from the linear-scanning ultrasonic transducer 2 and the radial-scanning ultrasonic transducer 3 are transmitted to an external ultrasonic signals processor (not shown) via cables 21 and 22, respectively. The external ultrasonic signals processor converts the input signals into corresponding image signals to input the same to a TV monitor 23. The TV monitor 23 displays an ultrasonic tomogram 24a obtained through the linear-scanning ultrasonic transducer 2 and an ultrasonic tomogram 24b obtained through the radial-scanning ultrasonic transducer 3 side by side at the same time, as shown in FIG. 1.

When the instrument 100 is operated to penetrate the needle 101 into a viscera or part of viscera which is located at the back or behind a mucous membrane, the tip of the instrument 100 passes the intersection "X" between the scanning plane section "A" and the scanning plane section "B". Therefore, the image of the tip of the instrument 100 appears in each of the ultrasonic tomograms 24a and 24b, which makes it possible to monitor the variation in penetration depth of the needle 101 on the ultrasonic tomogram 24a while monitoring the surroundings of the penetrated portion. Hence, an operation using the EUS of the present embodiment can be performed with safety.

The linear-scanning ultrasonic transducer 2 and the radial-scanning ultrasonic transducer 3 can be replaced by a biplane type ultrasonic transducer or probe, that is provided with a linear-scanning ultrasonic transducer and a radial-scanning ultrasonic transducer which are arranged overlapping each other. With such type of transducer, the correlation between the ultrasonic tomograms 24a and 24b can be easily recognized.

Obvious changes may be made in the specific embodiment of the present invention described herein, such modifications being within the spirit and scope of the invention claimed. It is indicated that all matter contained herein is illustrative and does not limit the scope of the present invention.

What is claimed is:

1. An ultrasonic endoscope comprising:
   an objective optical system provided at a tip portion of said ultrasonic endoscope;
   a treatment tool insertion channel provided along said ultrasonic endoscope, said treatment tool insertion channel having an exit opening at said tip portion;
   a linear-scanning ultrasonic transducer, provided at said tip portion, for scanning a first scanning plane section which lies on a plane including a shaft axis of said tip portion;
   a radial-scanning ultrasonic transducer, provided at said tip portion, for scanning a second scanning plane section which lies on a rotational plane about said shaft;
   a processor that converts output signals from both the linear-scanning and radial-scanning transducers into image signals for display,
   wherein said linear-scanning ultrasonic transducer and said radial-scanning ultrasonic transducer are positioned so that said first scanning plane section intersects said second scanning plane section within an optical field of said objective optical system, and
   wherein said treatment tool insertion channel is formed so that the tip of a tubular instrument, inserted into said treatment tool insertion channel, projects outwards from said exit opening to pass an intersection between said first scanning plane section and said second scanning plane section.

2. The ultrasonic endoscope according to claim 1, further comprising a display for simultaneously displaying a first image obtained through said linear-scanning ultrasonic transducer and a second image obtained through said radial-scanning ultrasonic transducer.

3. The ultrasonic endoscope according to claim 2, wherein said display comprises a TV monitor.

4. The ultrasonic endoscope according to claim 1, further comprising a device for moving said tip of said tubular instrument, which projects outwards from said exit opening, in a direction along said intersection.

5. The ultrasonic endoscope according to claim 4, wherein said moving device comprises a rotatable member which is positioned in the vicinity of said exit opening to abut against said tip of said tubular instrument.

6. The ultrasonic endoscope according to claim 1, wherein said linear scanning ultrasonic transducer and said radial-scanning ultrasonic transducer are arranged adjacent to each other so that said radial-scanning ultrasonic transducer is positioned closer to the distal end of said tip of said ultrasonic endoscope than the linear scanning ultrasonic transducer.

7. The ultrasonic endoscope according to claim 6, wherein said radial-scanning ultrasonic transducer is positioned so that said second scanning plane section is inclined rearwardly by a predetermined angle with respect to said shaft axis, and wherein said objective optical system is positioned so that the optical field of said objective optical system covers both said first scanning plane section and said second scanning plane section.

8. The ultrasonic endoscope according to claim 7, wherein said linear-scanning ultrasonic transducer is positioned between said radial-scanning ultrasonic transducer and said objective optical system, said objective optical system being positioned to extend an optical axis thereof forwardly towards said intersection.

9. The ultrasonic endoscope according to claim 8, wherein said objective optical system comprises a shield glass which is fixed to said tip portion adjacent to said exit opening.

10. The ultrasonic endoscope according to claim 8, wherein said shield glass is inclined by a predetermined angle with respect to said shaft axis to face said intersection.

11. An ultrasonic endoscope comprising:
    an objective optical system provided at a tip portion of said ultrasonic endoscope;
    a treatment tool insertion channel provided along said ultrasonic endoscope, said treatment tool insertion channel having an exit opening at said tip portion;
    a radial-scanning ultrasonic transducer, provided at said tip portion, for scanning one scanning plane section which lies on a rotational plane about a shaft axis of said tip portion;
    a linear-scanning ultrasonic transducer, provided at said tip portion to be positioned between said exit opening and said radial-scanning ultrasonic transducer, for scanning another scanning plane section which lies on a plane including said shaft axis,
    a processor that converts output signals from both the linear-scanning and radial-scanning transducers into image signals for display,
    wherein said linear-scanning ultrasonic transducer and said radial-scanning ultrasonic transducer are positioned so that said one scanning plane section intersects said another scanning plane section within an optical field of said objective optical system, and
    wherein said treatment tool insertion channel is formed so that the tip of a tubular instrument, inserted into said treatment tool insertion channel, projects outwards from said exit opening to pass an intersection between said one scanning plane section and said another scanning plane section.

12. The ultrasonic endoscope according to claim 11, further comprising a display for simultaneously displaying a first image obtained through said linear-scanning ultrasonic transducer and a second image obtained through said radial-scanning ultrasonic transducer.

13. The ultrasonic endoscope according to claim 12, wherein said display comprises a TV monitor.

14. The ultrasonic endoscope according to claim 11, further comprising a device for moving said tip of said tubular instrument, which projects outwards from said exit opening, in a direction along said intersection.

15. The ultrasonic endoscope according to claim 14, wherein said moving device comprises a rotatable member which is positioned in the vicinity of said exit opening to abut against said tip of said tubular instrument.

16. The ultrasonic endoscope according to claim 11, wherein said linear-scanning ultrasonic transducer and said radial-scanning ultrasonic transducer are arranged adjacent to each other so that said radial-scanning ultrasonic transducer is positioned closer to the distal end of said tip of said ultrasonic endoscope than the linear scanning ultrasonic transducer.

17. The ultrasonic endoscope according to claim 16, wherein said radial-scanning ultrasonic transducer is positioned so that said another scanning plane section is inclined rearwardly by a predetermined angle with respect to said shaft axis, and wherein said objective optical system is positioned so that the optical field of said objective optical system covers both said one scanning plane section and said another scanning plane section.

18. The ultrasonic endoscope according to claim 17, wherein said linear-scanning ultrasonic transducer is positioned between said radial-scanning ultrasonic transducer and said objective optical system, said objective optical system being positioned to extend an optical axis thereof forwardly towards said intersection.

19. The ultrasonic endoscope according to claim 18, wherein said objective optical system comprises a shield glass which is fixed to said tip portion adjacent to said exit opening.

20. The ultrasonic endoscope according to claim 18, wherein said shield glass is inclined by a predetermined angle with respect to said shaft axis to face said intersection.

\* \* \* \* \*